(12) United States Patent
Reimels

(10) Patent No.: US 10,299,845 B2
(45) Date of Patent: May 28, 2019

(54) ORTHOPEDIC SCREW

(71) Applicant: Alphatec Spine, Inc., Carlsbad, CA (US)

(72) Inventor: William Reimels, Oceanside, CA (US)

(73) Assignee: Alphatec Spine, Inc., Carlsbad, CA (US)

(*) Notice: Subject to any disclaimer, the term of this patent is extended or adjusted under 35 U.S.C. 154(b) by 332 days.

(21) Appl. No.: 14/875,308

(22) Filed: Oct. 5, 2015

(65) Prior Publication Data

US 2016/0095638 A1    Apr. 7, 2016

Related U.S. Application Data

(60) Provisional application No. 62/059,657, filed on Oct. 3, 2014.

(51) Int. Cl.
*A61B 17/86* (2006.01)

(52) U.S. Cl.
CPC ........ *A61B 17/8625* (2013.01); *A61B 17/869* (2013.01); *A61B 17/8685* (2013.01); *A61B 17/866* (2013.01)

(58) Field of Classification Search
CPC . A61B 17/869; F16B 25/0094; F16B 25/0031
See application file for complete search history.

(56) References Cited

U.S. PATENT DOCUMENTS 7,165,925 B2 *  1/2007  Unsworth ........... F16B 25/0031
411/16

* cited by examiner

*Primary Examiner* — Andrew Yang
(74) *Attorney, Agent, or Firm* — Honigman Miller Schwartz and Cohn LLP

(57) ABSTRACT

An orthopedic screw having a shaft and a thread ribbon is provided. The shaft includes a proximal driving end and a distal end. The thread ribbon extends around the shaft and including a base portion that is rigidly attached to the shaft and a flange portion that is resilient. The flange portion extends away from the shaft at a preset angle to form a preset outer thread diameter in a preset configuration. The flange portion extends away from the shaft at a second angle greater than the preset angle to form a second outer thread diameter greater than the preset outer thread diameter when the orthopedic screw is subjected to a pull out force.

20 Claims, 9 Drawing Sheets

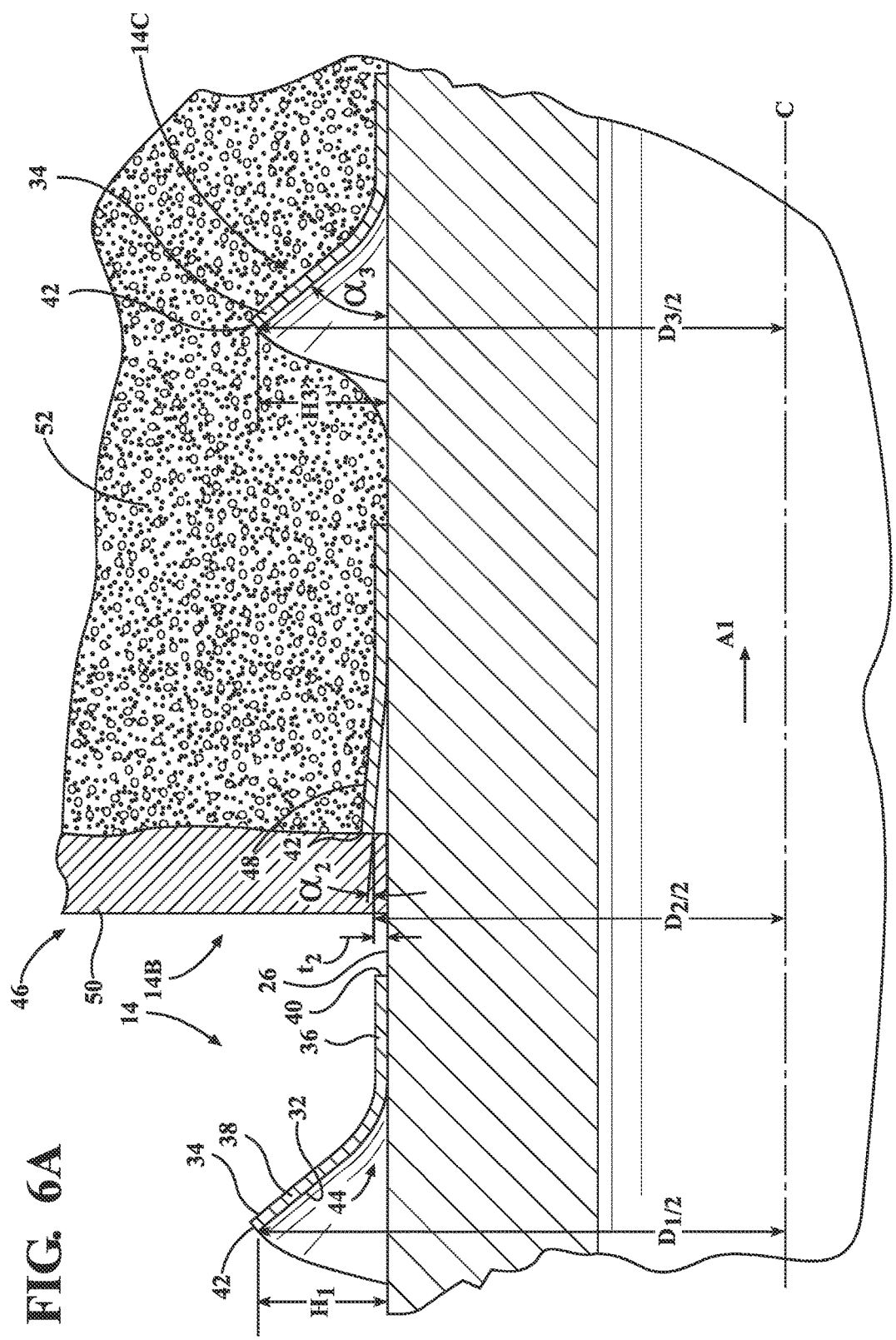

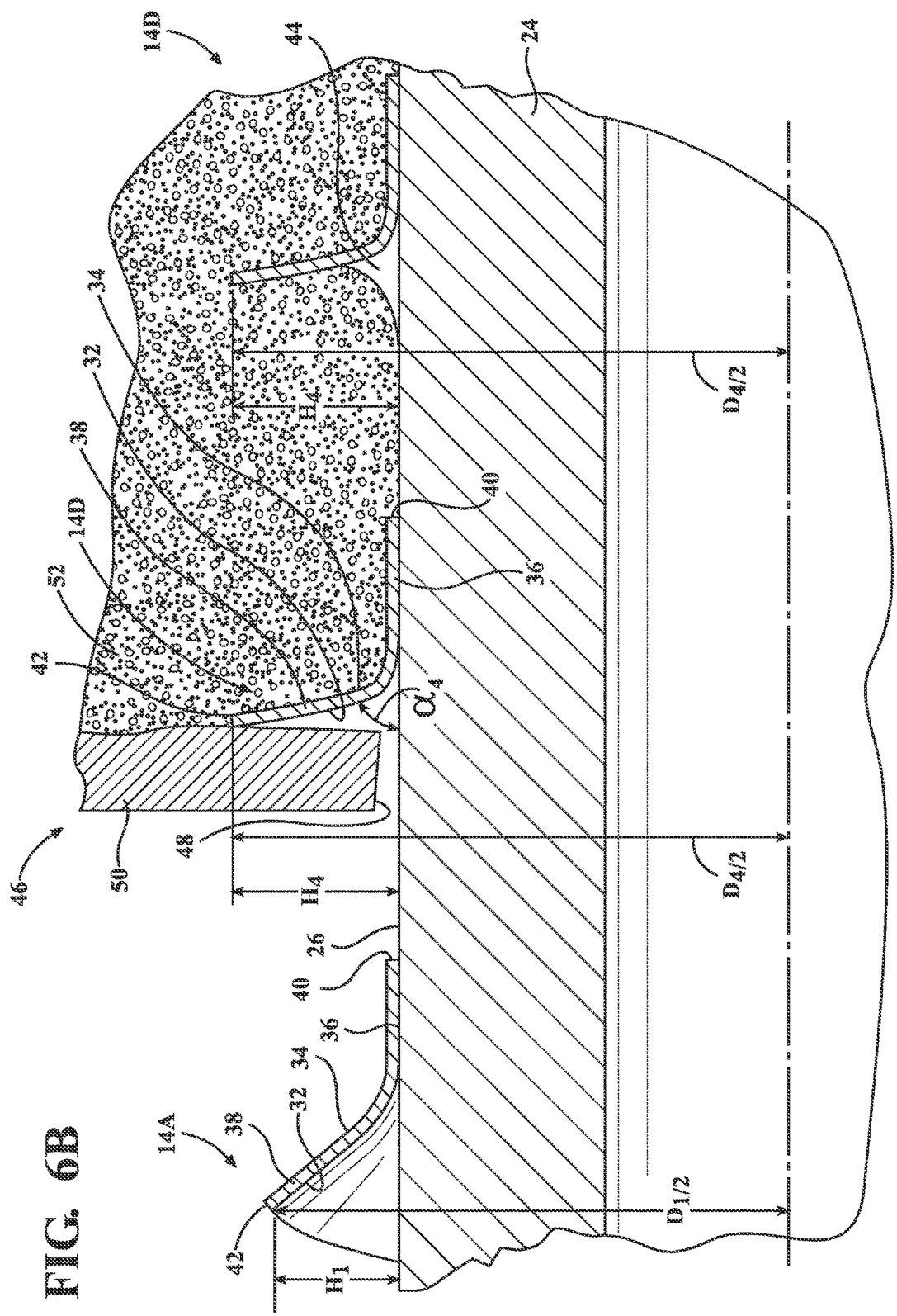

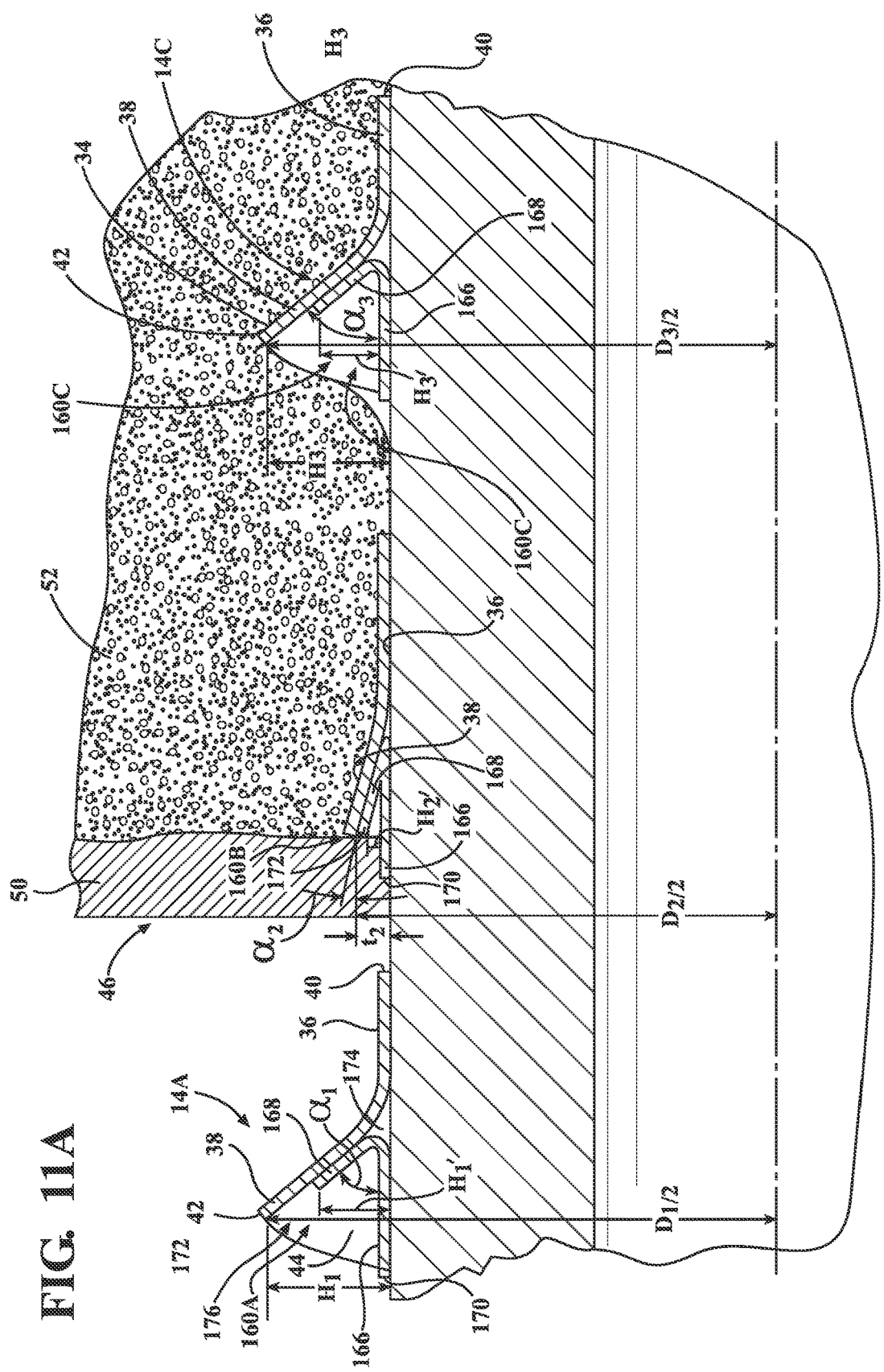

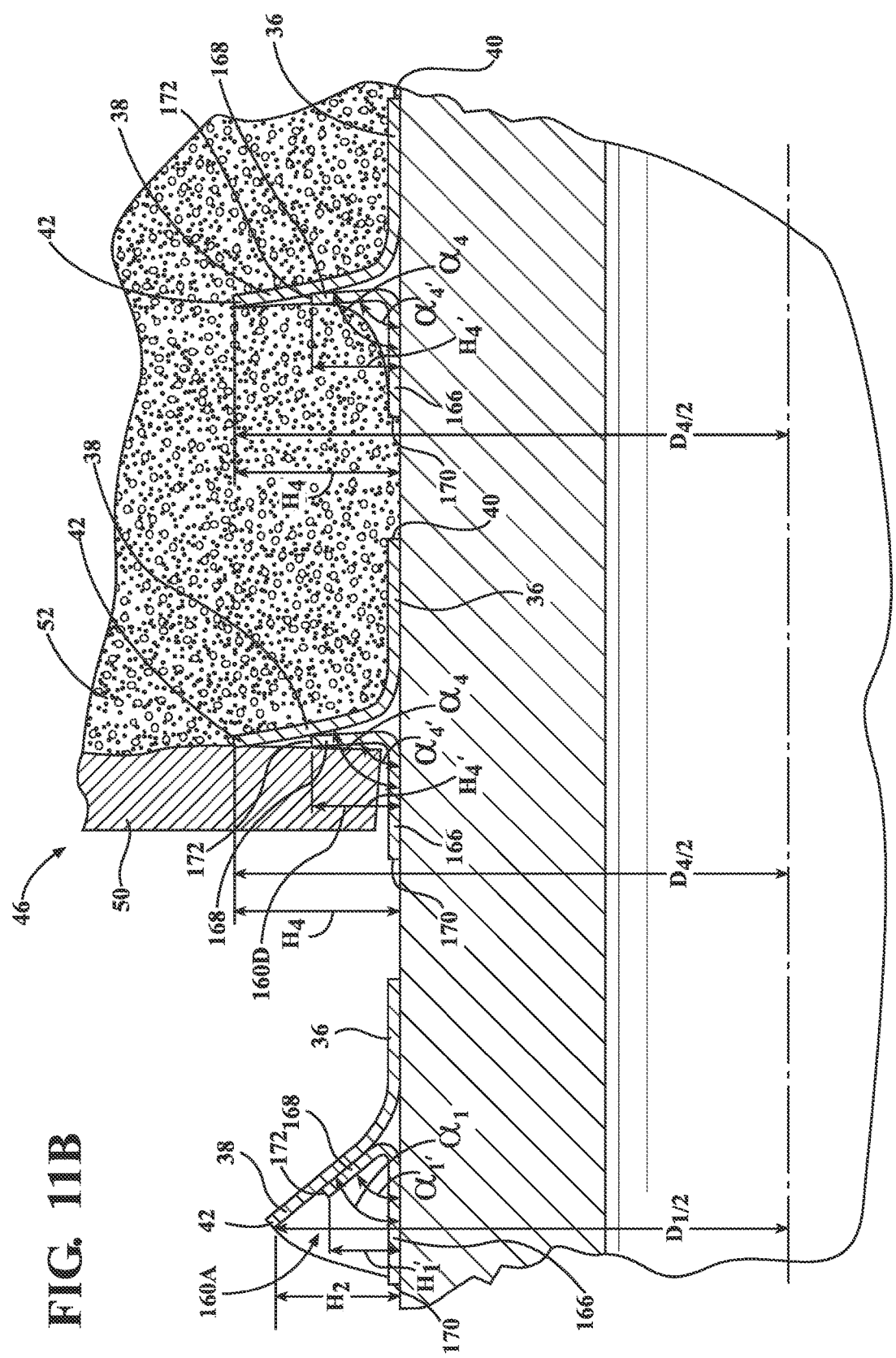

ORTHOPEDIC SCREW

CROSS-REFERENCE TO RELATED APPLICATIONS

This application claims priority of U.S. Provisional Application 62/059,657 filed Oct. 3, 2014, the contents of which are incorporated herein by reference.

FIELD OF THE INVENTION

An orthopedic screw for surgical procedures is provided. More particularly, the orthopedic screw is configured to have increased "pull out strength" while maintaining the ability for revisions to the screw site to facilitate subsequent procedures.

BACKGROUND OF THE INVENTION

Orthopedic screws are currently known and used for surgical procedures such as spinal fixation. Accordingly, it follows that fixation of an implant or fixation device is important. Fixation of the implant/fixation device is achieved by securing the implant or fixation device to the spine vis-à-vis the orthopedic screw.

As shown in FIG. 1, previously known orthopedic screws A include an external thread B extending around a screw shaft C. The threads B of the previously known screws A are formed having a solid cross-section with a generally triangular shape. Specifically, the space between the outermost end of the thread or "crest" D (the vertex of the triangular cross-section) and the shaft C of the screw contains some material.

Thus, the cross-section is filled-in with material. In some cases, this material may be a byproduct of the process by which the screw thread is generated. For example, it would be difficult to remove material in a cutting process at such an acute angle. In a rolling process, it is by nature impossible to remove the material. This material may provide strength to resist deformation of the thread or to prevent fracture of the shaft.

The threads B of the previously known orthopedic screws A may become loose after insertion into a patient and begin to exhibit a condition known as "pull out" in which the thread no longer engages enough bony material to provide rigid fixation. This may be due to the bone becoming weak or from the thread deforming in some manner to decrease the outer diameter such as rounding of the crest. As such, the screw may exhibit a decrease in "pull out strength" or the force required to pull the screw along its longitudinal axis and remove it from the bone without unscrewing. As used herein, "pull out strength" refers to the amount of force necessary to remove the orthopedic screw from the insertion site without rotation thereof.

Attempts have been made to improve the pull out strength of orthopedic screws. For instance, orthopedic screws have been manufactured with an expanding thread section. This expanding section may be formed of a mesh or expanding leafs that increases in diameter using a secondary deployment mechanism However, orthopedic screws with an expanding thread section may also be subject to failure. In some instances, the expanding thread section generates a weak point along the screw shaft. Further, screws with an expanding thread section may also be difficult to revise in a subsequent surgery due to bone ingrowth into the voids in the expanded thread section. The bone ingrowth locks the distal end of the screw in place and can prevent the collapse of the expanded section. When trying to remove an un-collapsed screw bone ingrowth can cause the distal end of the screw to fracture making complete screw removal difficult to achieve. Therefore, revisions to the screw site become problematic.

Thus, there exists a need in the art to improve the previously known orthopedic screws so as to increase a pull out strength while maintaining the ability for revisions to the screw site to facilitate subsequent procedures.

SUMMARY OF THE INVENTION

An orthopedic screw configured to have an increased a pull out strength, relative to conventional orthopedic screws, while maintaining the ability for revisions to the screw site to facilitate subsequent procedures is provided.

The orthopedic screw includes a shaft and a thread ribbon. The shaft includes a proximal driving end and a distal end. The thread ribbon extends around the shaft and includes a base portion that is rigidly attached to the shaft and a flange portion that is resilient. The flange portion extends away from the shaft at a preset angle to form a preset outer thread diameter in a preset configuration. The flange portion extends away from the shaft at a second angle greater than the preset angle to form a second outer thread diameter greater than the preset outer thread diameter when the orthopedic screw is subjected to a pull out force.

In other features, the orthopedic screw includes a reinforcement thread ribbon configured to reinforce the flange portion of the thread ribbon. The reinforcement thread ribbon includes a reinforcement base portion and a reinforcement flange portion. The reinforcement base portion is rigidly attached to the shaft. The reinforcement flange portion extends from the reinforcement base portion to an interior surface of the flange portion of the thread ribbon.

In another aspect of the pedicle screw, a plurality of weld spots are formed so as to achieve a desired rigidity of the thread ribbon.

BRIEF DESCRIPTION OF THE DRAWINGS

A better understanding of the present invention will be had upon reference to the following detailed description when read in conjunction with the accompanying drawings wherein like reference characters refer to like parts throughout the several views and in which:

FIG. 6A is an enlarged partial cross-sectional view of FIG. 5 illustrating the orthopedic screw in an inserted configuration;

FIG. 6B is an enlarged partial cross-sectional view of FIG. 5 illustrating the orthopedic screw in a pull out configuration;

FIG. 11A is an enlarged partial cross-sectional view of FIG. 10 illustrating the orthopedic screw of the second embodiment in an inserted configuration; and FIG. 11B is an enlarged partial cross-sectional view of FIG. 10 illustrating the orthopedic screw of the second embodiment in a pull out configuration;

DETAILED DESCRIPTION OF THE INVENTION

The embodiments described herein generally relate to an orthopedic screw having a shaft with a thread ribbon. The shaft includes a proximal driving end and a distal end. The thread ribbon includes a base portion and a flange portion. The base portion is rigidly secured to the shaft. The flange portion is may radially compress or expand relative to the base portion. The flange portion extends from the shaft at a first angle to provide the orthopedic screw with a first outer thread diameter in a first configuration. The flange portion extends from the shaft at a second angle to provide the orthopedic screw with a second outer thread diameter when subjected to a pull out force. The second outer thread diameter is greater than the first outer thread diameter. The increase in the outer thread diameter of the orthopedic screw increases the pull out strength required to remove the orthopedic screw from an insertion site without rotation.

Figure 2:
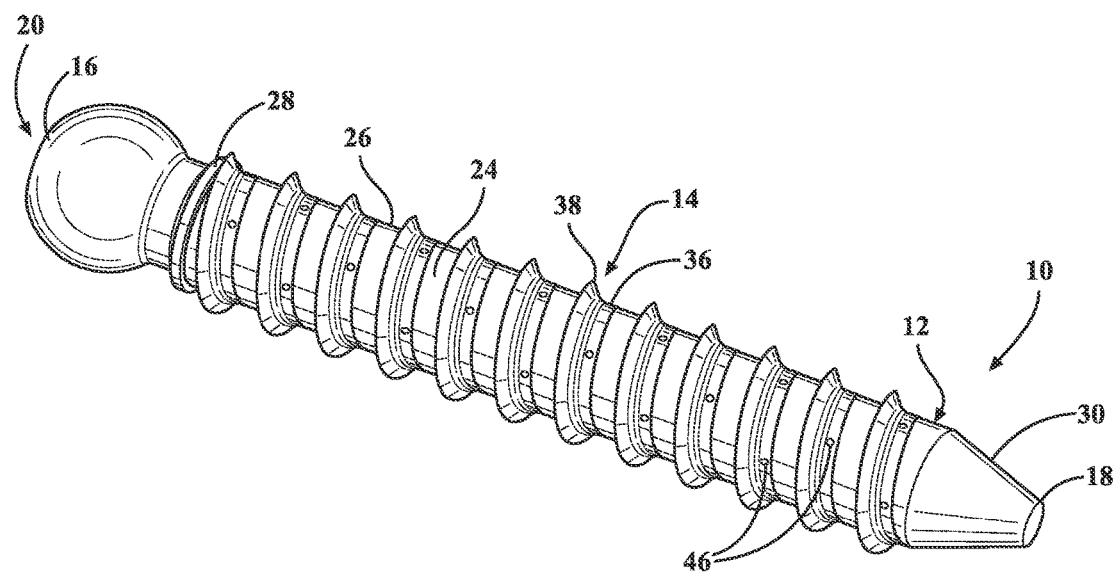
FIG. 2 is a perspective view of an orthopedic screw of a first embodiment.
Figure 3:
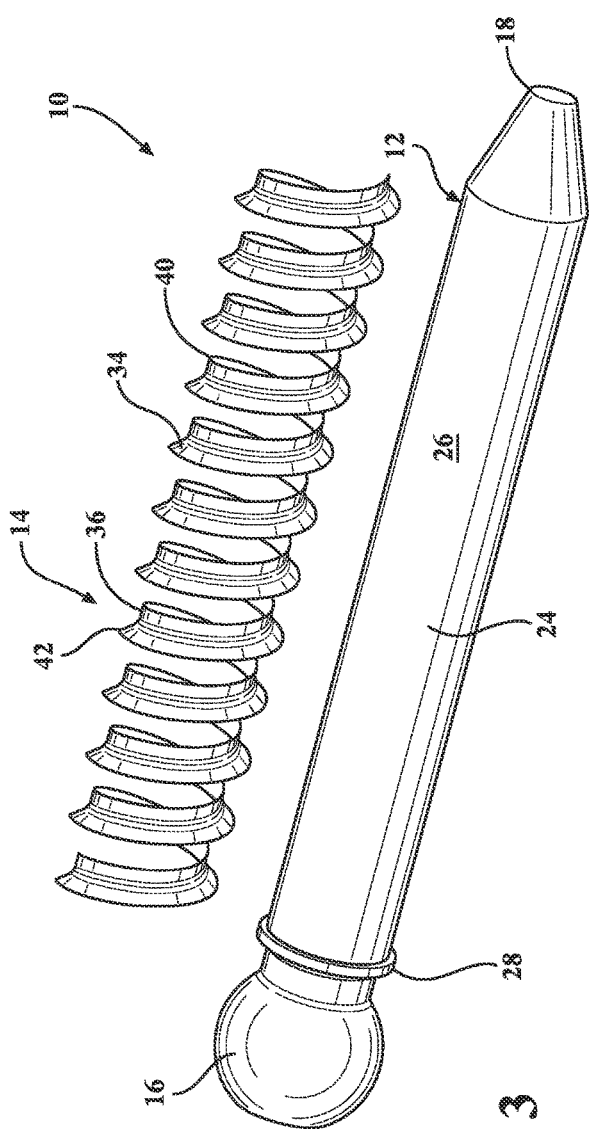
FIG. 3 is an exploded view of the orthopedic screw shown in FIG. 2.
Figure 4:
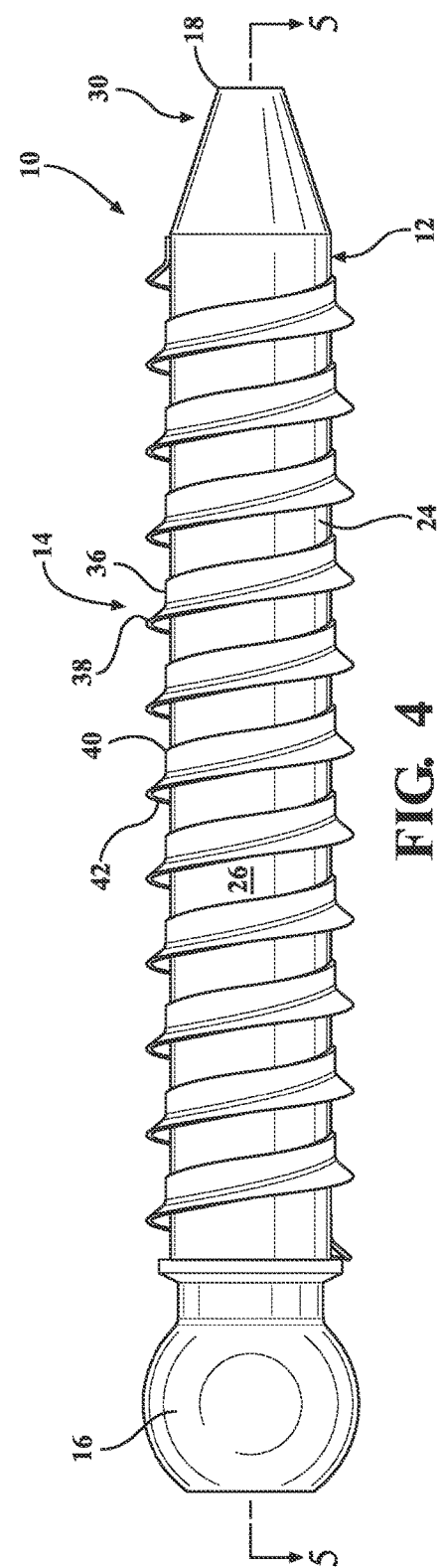
FIG. 4 is a top down view of the orthopedic screw shown in FIG. 2.
Figure 5:
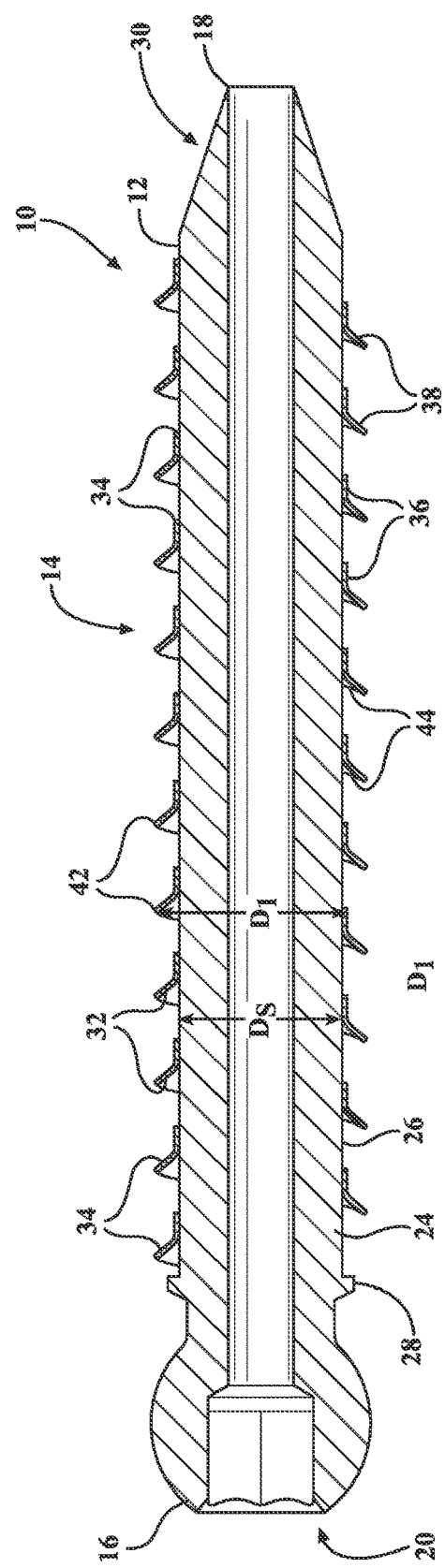
FIG. 5 is a cross-sectional view of the orthopedic screw of FIG. 4 taken along lines V-V.
Figure 7:
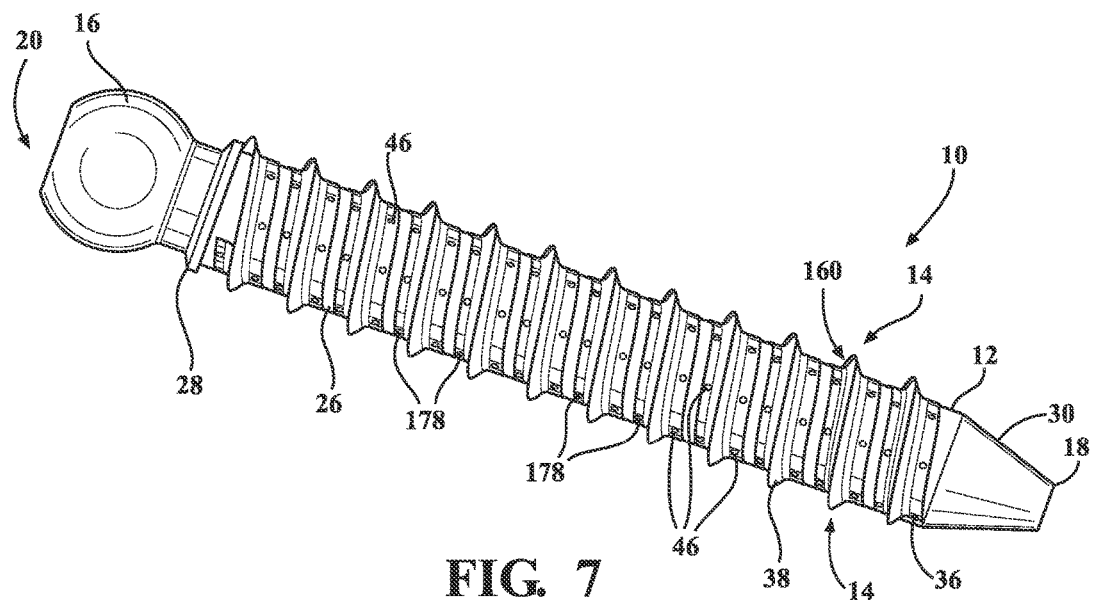
FIG. 7 is a perspective view of an orthopedic screw of a second embodiment.

With reference to FIGS. 2-4, an orthopedic screw is generally illustrated at 10. The orthopedic screw 10 includes a shaft 12 and a thread ribbon 14. The shaft 14 includes a proximal driving end 16 and a distal end 18. As best seen in FIG. 5, the proximate driving end 16 includes a head portion 20 adapted for receiving a correspondingly shaped tool.

In the illustrated embodiment, the shaft 12 is hollow shaft so as to form an interior passage 22 extending from the proximate driving end 16 to the distal end 18. It is appreciated, of course, that the shaft 12 is not limited to such a hollow configuration.

The shaft 12 includes a shank portion 24 having a generally cylindrical shape. The shank portion 24 is provided with an outer surface 26. The shank portion 24 extends from a collar 28 of the head portion 20 to the distal end 18. The head portion 20 is optionally formed spherical so as to rotate within a rod receiver (not shown). The head portion 20 includes a collar 28 extending radially outwardly therefrom. The collar 28 has a diameter larger than a diameter of the shank portion 24.

The distal end 18 may be tapered so as to have a generally frustoconical shape having a flat end surface. It is appreciated, of course, that the distal end portion 30 and the distal end 18 are not limited to such a configuration.

The thread ribbon 14 is formed having a helical shaped. The helical shape of the thread ribbon 14 corresponds to the generally cylindrical shape of the shank portion 24. As will be described in greater detail below, the thread ribbon 14 is rigidly secured to the outer surface 26 of the shank portion 24. The thread ribbon 14 is preferably formed as a one-piece elongated planar member.

With reference to FIG. 5, the thread ribbon 14 is formed having an interior surface 32 and an opposite exterior surface 34. The elongated planar member is bent along a longitudinal axis of the planar member so to form a bend 14a defining a base portion 36 and a flange portion 38 of the thread ribbon 14. The interior surface 32 of the base portion 36 is in contact with the outer surface 26 of the shank portion 24. The interior surface 32 of the flange portion 38 is spaced apart from the outer surface 26 of the shank portion 24 of the shaft 12.

The flange portion 38 extends away from the shank portion 24 of the shaft 12 at an angle. As will be described in greater detail below, the flange portion 38 is resilient.

The base portion 36 of the thread ribbon 14 includes a leading edge 40 that is provided facing the distal end 18. The flange portion 38 is provided with a trailing edge 42 that is facing the proximal driving end 16. The trailing edge 42 of the flange portion 38 is spaced apart from the outer surface 26 of the shank portion 24. The spacing of the trailing edge 42 forms a recess 44 between the outer surface 26 of the shank portion 24 and the interior surface 32 of the thread ribbon 14 of the flange portion 38.

The flange portion 38, specifically, the interior surface 32, forms an angle α1 with the outer surface 26 of the shank portion 24. The trailing edge 42 of the flange portion 38 is formed being spaced apart from the outer surface 26 of the shank portion 24 by a height H1.

With reference to FIG. 5, the angled orientation of the flange portion 38 and the spacing of the trailing edge 42 apart from the shaft 12, provides the orthopedic screw 10 with an outer thread diameter of D1. The outer thread diameter D1 is larger than a shaft diameter $D_S$ of the shank portion 24 of the shaft 12. As used herein, the 'outer thread diameter' refers to an outer diameter of the orthopedic screw 10 inclusive of the shank portion 24 and the thread ribbon 14 taking along a cross section perpendicular to a center longitudinal axis C of the orthopedic screw 10.

The flange portion 38 acts as a threaded portion for the orthopedic screw 10 and the base portion 36 acts as a securement to secure the thread ribbon 14 to the shaft 12. The thread ribbon 14 allows for the orthopedic screw 10 to be rotatably driven into a material, including bone.

The base portion 36 is rigidly attached to the outer surface 26 of the shank portion 24 of the shaft 12 by welding or the like, illustratively including laser welding. As the flange portion 38 is not directly connected to the outer 26 of the shank portion 24 of the shaft 12, the flange portion 38 is resilient. The degree of compression/expansion of the flange portion 38 is adjustable by adjusting the amount and spacing of the laser spots welds 46 coupling the base portion 36 to the shaft 12.

Specifically, by increasing a total number of welds 46 of the base portion 36 to the shaft 12 decreases the degree of compression/expansion afforded to the flange portion 38 relative to the shaft 12. Further, decreasing the amount of space between the weld 46 decreases the degree of compression/expansion afforded to the flange portion 38. Further still, increasing the distance between the weld 46 and the leading edge 40 decreases the degree of compression/expansion afforded to the flange portion 38.

As best illustrated in FIG. 2, the welds 46 are staggered and equally spaced along the length of the thread ribbon 14. It is appreciated, of course, that the placement and positioning of the welds 46 are not limited to the illustrated embodiment.

The thread ribbon 14 is formed of a resilient material configured facilitate the movement of the shaft 12 through different density layers of the bone and yet maintain a biased relationship when settled within the bone, and in which is also impervious to bone growth attachment, so as to prevent bone growth attachment to the thread ribbon 14 thus facilitating any surgical revision. The resilient material of the thread ribbon 14 illustratively includes stainless steel, nickel titanium alloy commonly referred to as Nitinol, or any other material having the above described properties.

With reference to FIG. 6A, the operation of the orthopedic screw 10 will now be discussed in greater detail. In FIG. 6A, an initial or preset configuration of the thread ribbon is generally illustrated at 14A. In the preset configuration, the flange portion 38 extends away from the shaft at preset angle α1, specifically, the interior surface 32 of the flange portion 38 extends away from the outer surface 26 of the shank portion 24 of the shaft 12 at preset angle α1. The trailing edge 42 of the flange portion 38 is spaced apart from the outer surface 26 of the shank portion 24 of the shaft 12 by preset height H1. In the preset configuration, the spacing of the trailing edge 42 of the flange portion 38 by the preset height H1 and the flange portion 38 extending away from the shaft at the preset angle α1 forms a preset outer thread diameter of D1, shown in radius form from the centered longitudinal axis C of the shaft 12.

During procedures, the orthopedic screw 10 is driven into a bone 46 of a patient. The orthopedic screw 10 is rotated to screw the orthopedic screw 10 into the bone along an insertion direction. The rotation of the orthopedic screw 10 facilitates engagement of the thread ribbon 14 with the bone 46.

Continued rotation and movement along the insertion direction of A1 causes a bore 48 to be formed in the bone 46. Specifically, the bore 48 is initially formed in a cortical layer 50 of the bone 46. The cortical layer 50 is an exterior layer of the bone 46. The density of the cortical layer 50 of the bone 46 compresses the segment of the thread ribbon 14 inserted into the bone 46, shown generally by 14B.

When compressed the flange portion 38 is provided with a compressed angle α2, specifically, the interior surface 32 of the flange portion 38 extends away from the outer surface 26 of the shank portion 24 of the shaft 12 at the compressed angle α2. The trailing edge 42 of the flange portion 38 is spaced apart from the outer surface 26 of the shank portion 24 of the shaft 12 by a compressed height H2. When compressed, the spacing of the trailing edge 42 of the flange portion 38 by the compressed height H2 and the flange portion 38 extending away from the shaft at the compressed angle α2 forms a compressed outer thread diameter of D2, shown in radius form from the centered longitudinal axis C of the shaft 12.

Figure 1:
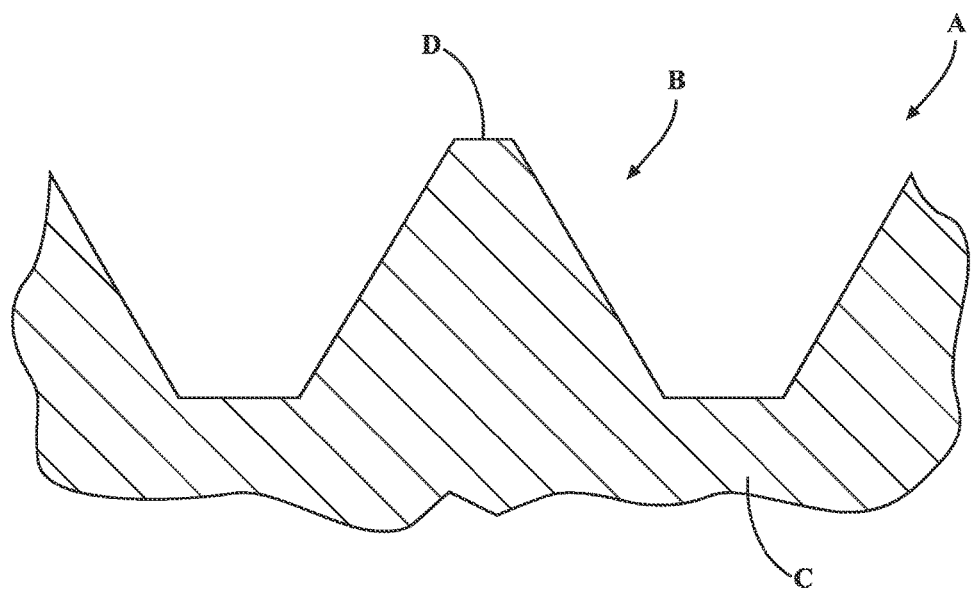
FIG. 1 is a partial cross-sectional view of the threads of a prior art orthopedic screw.

The compressed angle α2 is less than the preset angle α1 (α2<α1). The compressed height H2 is less than the preset height H1 (H2<H1), and the compressed outer thread diameter D2 is less than the preset outer thread diameter D1 (D2<D1). Accordingly, the orthopedic screw 10 having the thread ribbon 14 creates a smaller bore 48 relative to conventional threads B having triangular shaped cross sections as shown in FIG. 1.

Further rotation and movement along the insertion direction of A1 causes a segment of the thread ribbon 14 to extend into a cancellous layer 52 of the bone 46. The cancellous layer 52 is provided beneath the cortical layer 50. The cancellous layer 52 has a density that is less than the density of the cortical layer 50. Due to the reduction of density, moving from the cortical layer 50 to the cancellous layer 52, the segment of the thread ribbon 14 embedded in the cancellous layer 52 expands radially.

The thread ribbon engaged with the cancellous layer 52 is generally illustrated at 14C of FIG. 6A. The flange portion 38 is provided with an embedded angle α3, specifically, the interior surface 32 of the flange portion 38 extends away from the outer surface 26 of the shank portion 24 of the shaft 12 at the embedded angle α3. As such, the interior surface 32 of the flange portion 38 expands radially away from the outer surface 26 of the shank portion 24 of the shaft 12 to angle α3 The trailing edge 42 of the flange portion 38 is spaced apart from the outer surface 26 of the shank portion 24 of the shaft 12 by an embedded height H3.

When embedded in the cancellous layer 52, the spacing of the trailing edge 42 of the flange portion 38 by the embedded height H3 and the flange portion 38 extending away from the shaft at the embedded angle α3 forms an embedded outer thread diameter of D3, shown in radius form from the centered longitudinal axis C of the shaft 12.

The embedded angle α3 is greater than the compressed angle α2 and less than or equal to the preset angle α1 (α3>α2, α3≤α1). The embedded height H3 is greater than the compressed height H2 and is less than or equal to the preset height H1 (H3>H2, H3≤H1), and the embedded outer thread diameter D3 is greater than the compressed outer thread diameter D2 and is less than or equal to the preset outer thread diameter D1 (D3>D2, D3≤D1).

With reference to FIG. 6B, upon application of a pull out force along a retraction direction A2, the segment of the thread ribbon 14 embedded into the bone 46 moves to an expanded configuration. The retraction direction A2 is opposite the insertion direction A1, both of which extend along the center longitudinal axis C of the orthopedic screw 10. The pull out force is a force in the retraction direction A2 without rotation of the orthopedic screw 10.

Upon application of the pull out force, the orthopedic screw 10 is pulled in the retraction direction of A2. The movement of the orthopedic screw 10 in the retraction direction A2 causes the recess 44 to engage with the at least one of the cancellous layer 52 and cortical layer 50 of the bone 46. The continued application of the pull out force in the retraction direction radially expands the flange portion 38 of the segment of the thread ribbon 14 inserted into the bone 46. Specifically, when subject to a pull out force in the retraction direction, the flange portion 38 is captured in the bone 46 and expands radially outward relative to the shaft 12 causing the effective diameter of the orthopedic screw 10 to increase.

14D of FIG. 6B shows the threaded ribbon in an expanded position. The flange portion 38 is expanded to angle α4, specifically, the interior surface 32 of the flange portion 38 extends away from the outer surface 26 of the shank portion 24 of the shaft 12 at the expanded angle α4. The trailing edge 42 of the flange portion 38 is spaced apart from the outer surface 26 of the shank portion 24 of the shaft 12 by an expanded height H4.

When expanded, the spacing of the trailing edge 42 of the flange portion 38 by the expanded height H4 and the flange portion 38 extending away from the shaft at the expanded angle α4 forms an expanded outer thread diameter of D4, shown in radius form from the centered longitudinal axis C of the shaft 12.

The expanded angle α4 is greater than the embedded angle α3, the compressed angle α2 and the preset angle α1 (α4>α3, α4>α2, α4>α1). The expanded height H4 is greater than the embedded height H3, the compressed height H2, and the preset height H1 (H4>H3, H4>H2, H4>H1). The expanded outer thread diameter D4 is greater than the embedded outer thread diameter D3, the compressed outer thread diameter D2, the preset outer thread diameter D1 (D4>D3, D4>D2, D4>D1).

The increase in the outer thread diameter to the expanded outer thread diameter D4 increases the effective screw diameter which improves a pull out strength of the orthopedic screw 10. The increase in screw diameter increases a frictional resistance to the movement of the orthopedic screw 10 in the retraction direction A2 when undergoing a pull out force. The expansion of the flange portion 38 maintains the ability of the orthopedic screw 10 to be removed by rotation, thereby allowing revisions to the screw site.

With reference to FIGS. 7-10, the orthopedic screw 110 is provided with a reinforcement thread ribbon 160. The reinforcement thread ribbon 160 is formed having a helical shape. The helical shape of the reinforcement thread ribbon 160 corresponds to the generally cylindrical shape of the shank portion 24 and the helical shape of the thread ribbon 14. The reinforcement thread ribbon 160 is optionally formed as a one-piece elongated planar member. As will be described in greater detail below, the reinforcement thread ribbon 160 is rigidly secured to the outer surface 26 of the shank portion 24 of the shaft 12.

The reinforcement thread ribbon 160 is formed having an interior surface 162 and an opposite exterior surface 164. The elongated planar member is bent along a longitudinal axis of the planar member so as to form a bend 14a defining a reinforcement base portion 166 and a reinforcement flange portion 168 of the reinforcement thread ribbon 160. The interior surface 162 of the reinforcement base portion 166 is in contact with the outer surface 26 of the shank portion 24 of the shaft 12. The interior surface 162 of the reinforcement flange portion 168 extends radially from the reinforcement base portion 166. The reinforcement flange portion 168 extends away from the shank portion 24 of the shaft 12 at an angle. As will be described in greater detail below, the reinforcement flange portion 168 is resilient The reinforcement base portion 166 of the reinforcement thread ribbon 160 includes a trailing edge 170 that faces the proximal driving end 16. The reinforcement flange portion 168 is provided with an abutment edge 172 that faces the distal end 18. The abutment edge 172 of the reinforcement flange portion 168 is spaced apart from the outer surface 26 of the shank portion 24.

The reinforcement base portion 166 is rigidly attached to the outer surface 26 of the shank portion 24 of the shaft 12 by welding or the like, illustratively including laser welding. The abutment edge 172 of the reinforcement flange portion 168 contacts the interior surface 32 of the flange portion 38 of the thread ribbon 14.

The thread ribbon 14 and the reinforcement thread ribbon 160 are helically provided around the shank portion 24 such the trailing edge 170 of the reinforcement base portion 166 is spaced apart from the leading edge 40 of the base portion 36 a prior winding.

The spacing of the abutment edge 172 forms a cavity 174 between the outer surface 26 of the shank portion 24, and the interior surface 32 of the thread ribbon 14 of the flange portion 38 and the interior surface 162 of the reinforcement flange portion 168 of the reinforcement thread ribbon 160, as best seen in FIGS. 11A and 11B.

The reinforcement flange portion 168 acts as a reinforcement for the flange portion 38 of the threaded portion 14. As will be described in greater detail below, the reinforcement flange portion 168 prevents the flange portion 38 from being in contact with the outer surface 26 of the shank potion 24 of the shaft 12 when compressed.

Figure 9:
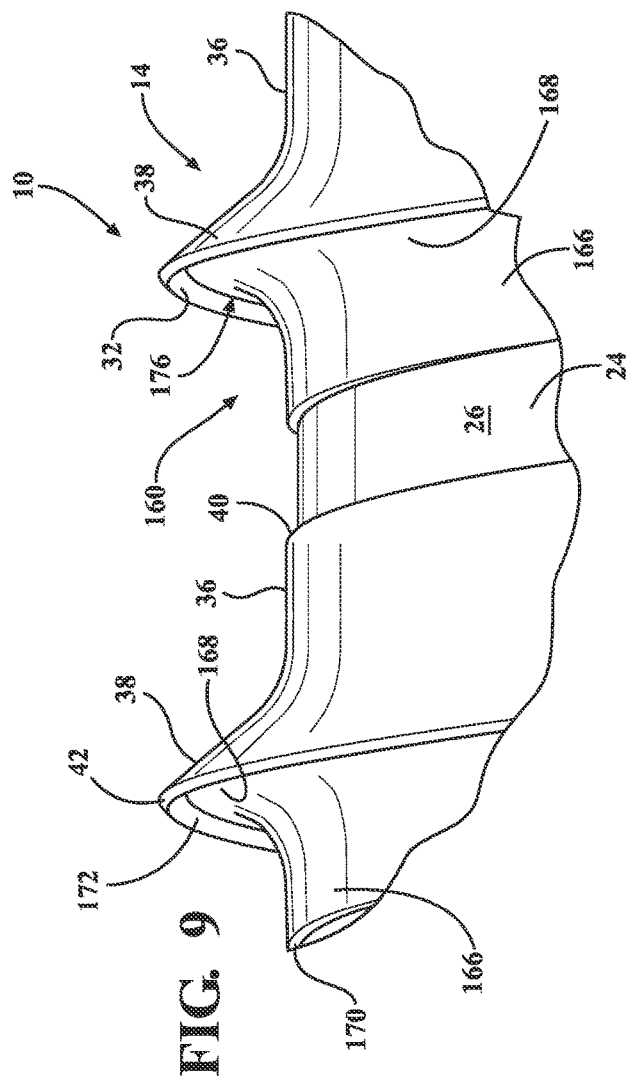
FIG. 9 is an isolated view of the orthopedic screw annotated by IX in FIG. 7.
Figure 10:
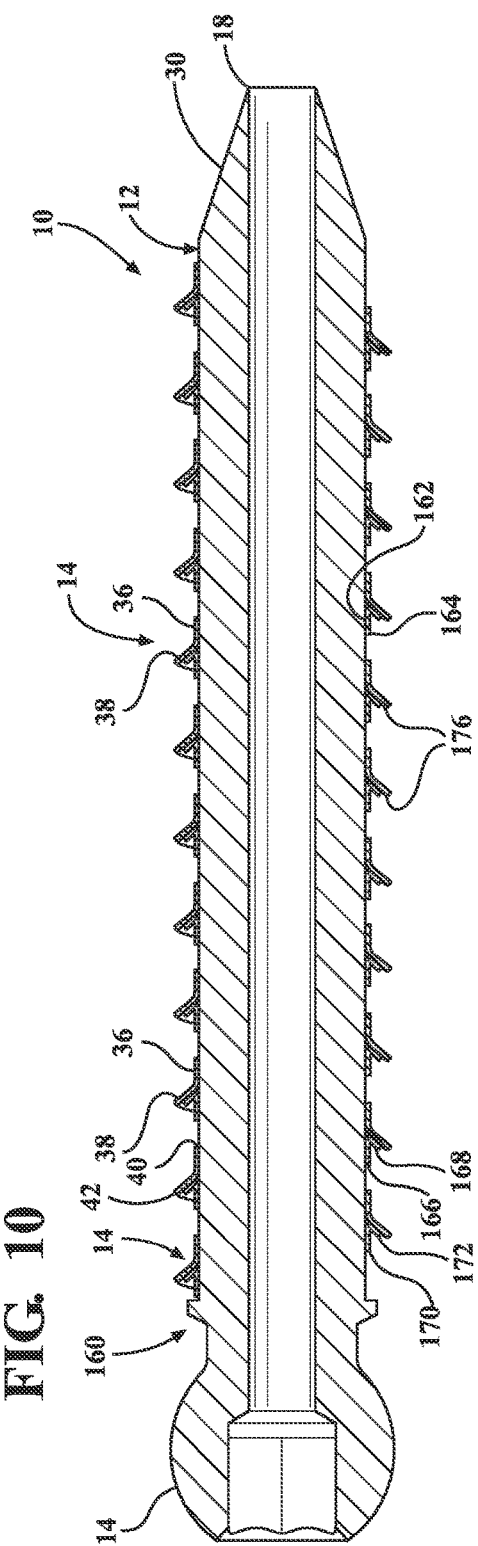
FIG. 10 is a cross-sectional view of the orthopedic screw of FIG. 7 taken along line X-X.

The flange portion 38 is formed radially longer than the reinforcement flange portion 168. As illustrated in FIG. 9, the trailing edge 42 of the flange portion 38 extends beyond the abutment edge 172 of the reinforcement flange portion 168 so as to form a rim 176.

The reinforcement flange 168 is resilient. The degree of compression/expansion of the reinforcement flange portion 168 is adjustable by adjusting the amount and spacing of the welds 178 coupling the reinforcement base portion 166 to the shaft 12.

Specifically, by increasing a total number of welds 178 of the reinforcement base portion 166 to the shaft 12 decreases the degree of compression/expansion afforded to the reinforcement flange portion 168 relative to the shaft 12. Further, decreasing the amount of space between the weld 178 decreases the degree of compression/expansion afforded to the reinforcement flange portion 168. Further still, increasing the distance between the weld 178 and the trailing edge 170 decreases the degree of compression/expansion afforded to the reinforcement flange portion 168.

Figure 8:
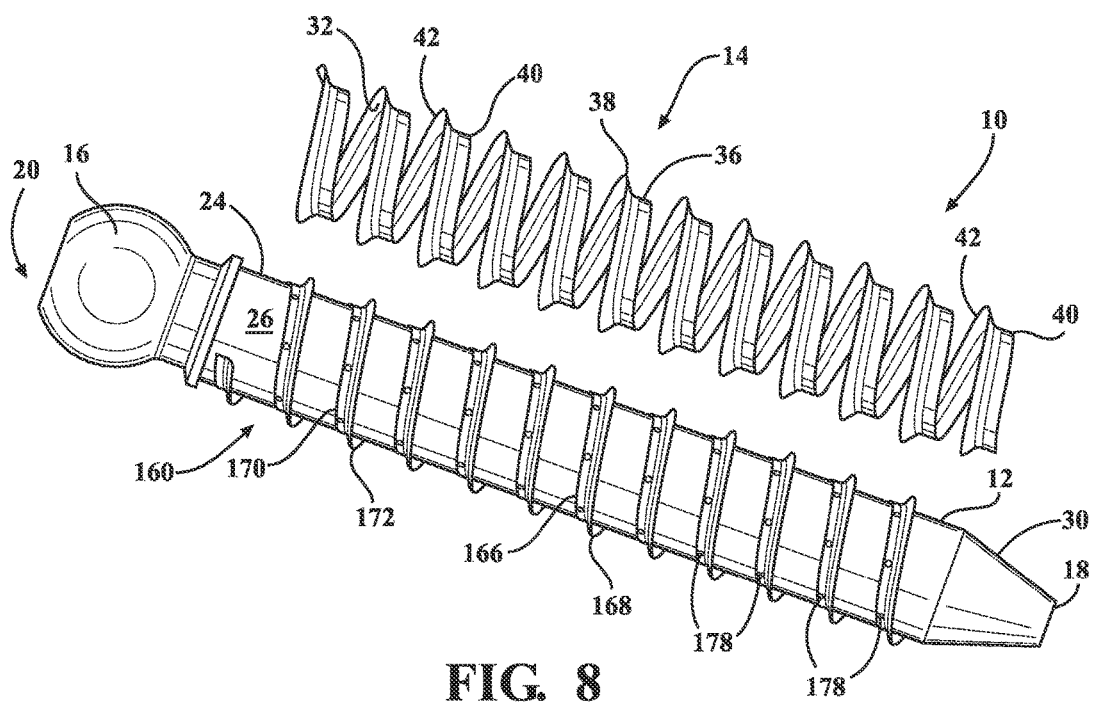
FIG. 8 is a partially exploded view of the orthopedic screw shown in FIG. 7.

As best illustrated in FIG. 8, the welds 178 are staggered and equally spaced along the length of the reinforcement thread ribbon 160. It is appreciated, of course, that the placement and positioning of the welds 178 are not limited to the illustrated embodiment.

The abutment edge 172 of the reinforcement flange portion 138 is rigidly attached to the interior surface 32 of the flange portion 38 of the thread ribbon 14, by laser welding or the like. Alternatively, the abutment edge 172 of the reinforcement flange portion 138 is optionally unattached to the interior surface 32 of the flange portion 38 of the thread ribbon 14

The reinforcement thread ribbon 160 is formed of a resilient material configured facilitate the movement of the shaft 12 through different density layers of the bone and yet maintain a biased relationship when settled within the bone, and in which is also impervious to bone growth attachment, so as to prevent bone growth attachment to the reinforcement thread ribbon 160 thus facilitating any surgical revision. The resilient material of the reinforcement thread ribbon 160 illustratively includes stainless steel, nickel titanium alloy commonly referred to as Nitinol, or any other material having the above described properties.

With reference to FIG. 11A, the operation of the orthopedic screw 110 will now be described in greater detail. The thread ribbon 14 in the preset configuration of 14A and the embedded configuration of 14C operate in a similar manner as described above in relation to FIG. 6A.

Upon continued rotation and movement along the insertion direction of A1 causes a bore 48 to be formed in the bone 46. The density of the cortical layer 50 of the bone 46 compresses the segment of the thread ribbon 14 inserted into the bone 46, as shown generally by 14B. When compressed, the reinforcement flange portion 168 prevents the flange portion 38 from compressing entirely such that the interior surface 32 of the flange portion 38 contacts the outer surface 26. Due to the placement of the reinforcement flange portion 168, the flange portion 38 is prevented from contacting the outer surface 26 of the shank portion 24 of the shaft 12, as best seen in FIG. 11A.

Further, due to the flange portion 38 extending beyond the reinforcement flange portion 168, the rim 176 acts as the recess to capture the bone 46 to move to the expanded position as seen in FIG. 11B.

Similar to the thread ribbon 14, the reinforcement thread ribbon 160 is positioned in a preset configuration 160A, compressed in 160B, embedded 160C, and expanded 160D, shown in FIGS. 11A-11B.

In the preset configuration 160A, the reinforcement flange portion 168 is provided with a preset angle $\alpha 1'$, specifically, the interior surface 162 of the reinforcement flange portion 168 extends away from the outer surface 26 at the preset angle α1'. The trailing edge 170 of the reinforcement flange portion 168 is spaced apart from the outer surface 26 of the shank portion 24 of the shaft 12 by a preset height H1'.

When compressed, the reinforcement flange portion 168 is provided with a compressed angle α2', specifically, the interior surface 162 of the reinforcement flange portion 168 extends away from the outer surface 26 at the compressed angle α2'. The trailing edge 170 of the reinforcement flange portion 168 is spaced apart from the outer surface 26 of the shank portion 24 of the shaft 12 by a compressed height H2'. The compressed angle α2' is less than the preset angle α1' (α2'<α1'). The compressed height H2' is less than the preset height H1' (H2'<H1').

When embedded in the cancellous layer 52, as shown at 160C, the reinforcement flange portion 168 is provided with an embedded angle α3', specifically, the interior surface 162 of the reinforcement flange portion 168 extends away from the outer surface 26 at the embedded angle α3'. The trailing edge 170 of the reinforcement flange portion 168 is spaced apart from the outer surface 26 of the shank portion 24 of the shaft 12 by an embedded height H3'. The embedded angle α3' is less than or equal to the preset angle α1' and the compressed angle α2' (α3'≤α1', α3'>α2'). The embedded height H3' is greater than the compressed height H2' and less than or equal to the preset height H1'(H3'>H2, H3'≤H1').

When expanded, as shown at 160D, the reinforcement flange portion 168 is provided with an expanded angle α4', specifically, the interior surface 162 of the reinforcement flange portion 168 extends away from the outer surface 26 at the expanded angle α3'. The trailing edge 170 of the reinforcement flange portion 168 is spaced apart from the outer surface 26 of the shank portion 24 of the shaft 12 by an expanded height H4'. The expanded angle α4' is greater than the embedded angle α3', the compressed angle α2' and the preset angle α1' (α4'>α3', α4'>α2', α4'>α1'). The expanded height H4' is greater than the embedded height H2', the compressed height H2' and the preset height H1' (H4'>H3', H4'>H2', H4'>H1').

The expanded position of the thread ribbon corresponds to the 'second configuration' such that the expanded angle α4 corresponds to the "second angle" and the expanded outer thread diameter corresponds to the "second outer thread diameter".

The orthopedic screw is configured for use in various orthopedic procedures illustratively including spinal fusion and spinal deformity, and uses illustratively including a pedicle screw, a fixation screw, and a plate screw.

It should be appreciated that the description provided herein is not limiting to the concept of set forth in the claims. For instance, the thread ribbon 14 optionally includes different profiles to provide different preset angles of the flange portion relative to the outer surface 26. In addition, the orthopedic screw 10 optionally includes multiple discontinues thread ribbons 14 used to form multi start threads or threads with or without a reinforcement thread ribbon.

It is claimed:

1. An orthopedic screw comprising:
a shaft having a proximal driving end and a distal end; and
a thread ribbon extending around the shaft and including a base portion that is rigidly attached to the shaft and a flange portion that is resilient and integrally formed to the base portion and extending radially from the base portion,
the flange portion extends away from the shaft at a preset angle to form a preset outer thread diameter in a preset configuration; and
the flange portion extends away from the shaft at a second angle greater than the preset angle to form a second outer thread diameter greater than the preset outer thread diameter when the orthopedic screw is subjected to a pull out force.

2. The orthopedic screw of claim 1, wherein the shaft includes a generally cylindrical shank portion having an outer surface, and wherein the base portion of the thread ribbon is rigidly attached to the outer surface of the shank portion.

3. The orthopedic screw of claim 2, wherein the thread ribbon extends helically around the shank portion of the shaft from a portion adjacent the distal end to a portion adjacent the proximal driving end.

4. The orthopedic screw of claim 3, wherein the thread ribbon is a one-piece elongated planar member.

5. The orthopedic screw of claim 4, wherein the thread ribbon is bent along a longitudinal axis of the one-piece elongated planar member so to form a bend, the bend defining the flange portion and the base portion.

6. The orthopedic screw of claim 5, wherein the preset angle is formed between the outer surface of the shank portion and an interior surface of the flange portion in the preset configuration, and wherein the second angle is between the outer surface of the shank portion and the interior surface of the flange portion when the orthopedic screw is subjected to a pull out force.

7. The orthopedic screw of claim 6, wherein the flange portion of the segment of the thread ribbon inserted into a bone expands radially relative to the shaft when subjected to the pull out force.

8. The orthopedic screw of claim 7, wherein the base portion of the thread ribbon is rigidly attached to the shaft by a plurality of spot welds.

9. The orthopedic screw of claim 8, wherein the plurality spot welds are equally spaced apart from each other.

10. The orthopedic screw of claim 5, further comprising a reinforcement thread ribbon that is configured to reinforce the flange portion of the thread ribbon.

11. The orthopedic screw of claim 10, wherein the reinforcement thread ribbon includes a reinforcement base portion and a reinforcement flange portion, the reinforcement base portion is rigidly attached to the shaft, the reinforcement flange portion extends from the reinforcement base portion to the interior surface of the flange portion.

12. The orthopedic screw of claim 11, wherein the reinforcement thread ribbon extends helically around the shank portion of the shaft.

13. The orthopedic screw of claim 12, wherein the reinforcement thread ribbon is formed as a one-piece elongated planar member.

14. The orthopedic screw of claim 13, wherein the reinforcement thread ribbon is bent along a longitudinal axis of the one-piece elongated planar member so to form a bend, the bend defining the reinforcement flange portion and the reinforcement base portion.

15. The orthopedic screw of claim 14, wherein the base portion of the thread ribbon is rigidly attached to the shaft by a plurality of spot welds, and wherein the base portion of the reinforcement thread ribbon is rigidly attached to the shaft by a plurality of spot welds.

16. The orthopedic screw of claim 15, wherein the plurality of spot welds on the base portion of the thread ribbon are equally spaced, and wherein the plurality of spot welds on the base portion of the reinforcement thread ribbon are equally spaced.

17. The orthopedic screw of claim 10, wherein the reinforcement thread ribbon is composed of Nitinol.

18. The orthopedic screw of claim 10, wherein the reinforcement thread ribbon is composed of stainless steel.

19. The orthopedic screw of claim 1, wherein the thread ribbon is composed of Nitinol.

20. The orthopedic screw of claim 1, wherein the thread ribbon is composed of stainless steel.

* * * * *